United States Patent [19]

Schaefer et al.

[11] Patent Number: 5,149,882
[45] Date of Patent: Sep. 22, 1992

[54] PURIFICATION OF 2-CHLORO-5-NITROBENZALDEHYDE OR ACETALS THEREOF

[76] Inventors: Bernd Schaefer, 22 Hauptstrasse, 6749 Dierbach; Wolfgang Freund, 71 Johann-Gottlieb-Fichte-Strasse, 6730 Neustadt; Gernot Reissenweber, 15 Drosselstrasse, 6737 Boehl-Iggelheim, all of Fed. Rep. of Germany

[21] Appl. No.: 709,855

[22] Filed: Jun. 4, 1991

[30] Foreign Application Priority Data

Jun. 15, 1990 [DE] Fed. Rep. of Germany ....... 4019049

[51] Int. Cl.$^5$ .................. C07C 45/78; C07C 45/80
[52] U.S. Cl. .................. 568/438; 568/426; 568/436
[58] Field of Search ............... 568/424, 426, 435, 438, 568/436

[56] References Cited

U.S. PATENT DOCUMENTS 4,506,089  7/1986  Hackenburger et al. .
4,714,783 12/1987  Zinnen et al. ........................ 568/424
4,910,345  3/1990  Streicher et al. ..................... 568/424

FOREIGN PATENT DOCUMENTS 0061113  9/1982  European Pat. Off. ............ 568/424
0118862  9/1984  European Pat. Off. .
0305812  3/1989  European Pat. Off. ............ 568/424
3728826  3/1989  Fed. Rep. of Germany .
3017851  1/1988  Japan .................................. 568/424

OTHER PUBLICATIONS

Monatsheft, vol. 25, pp. 365–374 (1904).
Liebigs Ann., vol. 272, pp. 148–150 (1983).
Journal of the Chemical Society, *Chloro-derivatives of m-hydroxybenzaldehyde*, Herbert H. Hodgson & Herbert G. Beard, Jan. 1926, pp. 147–155.
Monatshefte fur Chemie, *Uber substituierte Benzaldehyde*, Paul Cohn & Albert Blau, pp. 365–374.

*Primary Examiner*—Werren B. Lone
*Attorney, Agent, or Firm*—Keil & Weinkauf

[57] ABSTRACT

2-chloro-5-nitrobenzaldehyde or an acetal thereof is isolated from a mixture of isomers thereof at a temperature of from −10° to +140° C., by suspending the mixture of isomers in a solvent or solvent mixture.

8 Claims, No Drawings

PURIFICATION OF 2-CHLORO-5-NITROBENZALDEHYDE OR ACETALS THEREOF

The present invention relates to a method of isolating pure 2-chloro-5-nitrobenzaldehyde or an acetal thereof from a mixture of its isomers by forming a suspension of the latter at a temperature of from −10° to +140° C.

Monatsheft Vol. 25, pp. 365-374 (1904) discloses that the synthesis of 2-chloro-5-nitrobenzaldehyde leads to a product which is contaminated by a second isomer: 2-chloro-3-nitrobenzaldehyde.

Purification of the target product, 2-chloro-5-nitrobenzaldehyde, may be effected by recrystallization thereof from a variety of solvents, for example from dilute ethanol, chloroform/ligroin as described in Liebigs Ann., Vol. 272, pp. 148-150 (1983), or dilute acetic acid as described in J. Chem. Soc., pp. 147-155 (1926). This is a very laborious procedure, which may have to be repeated (cf. Liebigs Ann., Vol. 272, pp. 147-157 (1893). Furthermore, there are considerable losses of target product, and extensive quantities of solvent are necessary. In large-scale production, therefore, additional measures must be taken to effect solvent recovery.

DE-A 3,728,826 describes the purification of m-nitrobenzaldehyde with water in the presence of an emulsifying agent by refluxing the suspension.

This method suffers from the drawbacks that it is usually necessary to heat the suspension to reflux temperature in order to obtain a homogeneous suspension and that the aqueous phase from the purifying stage contains the undesirable positional isomer and the emulsifying agent, which is not entirely harmless toxicologically.

Moreover, the method fails completely in attempts to use it for purifying 2-chloro-5-nitrobenzaldehyde.

It is thus an object of the present invention to overcome the above drawbacks.

Accordingly, we have found a novel and improved method of isolating pure 2-chloro-5-nitrobenzaldehyde or an acetal thereof from a mixture of its isomers at a temperature of from −10° to +140° C., wherein the said mixture of isomers is suspended in a solvent or solvent mixture.

The method of the invention is characterized in that the mixture of chloronitrobenzaldehyde isomers (2,5- and 2,3-isomers) or acetals thereof is purified in the form of a suspension. By "suspension" (cf. Roempp Lexikon) is meant a heterogeneous mixture consisting of a liquid phase and a solid phase in various proportions.

According to the invention, the proportion of solids in the suspension is from 50 to 99% w/w, preferably from 60 to 98% w/w, and more preferably from 70 to 95% w/w, based on the dry weight of the mixture of chloronitrobenzaldehyde isomers or acetals thereof to be treated.

The solvents used may be divided into two groups:

Group A: $C_1$–$C_{20}$-alkanols, preferably $C_1$–$C_8$-alkanols, more preferably $C_1$–$C_4$-alkanols, for example, methanol, ethanol, n-propanol, and isopropanol; ketones, for example acetone, diethyl ketone, and ethylmethyl ketone; esters, for example ethyl acetate and methyl acetate; ethers, preferably cyclic ethers, for example tetrahydrofuran and tetrahydropyran; aromatic hydrocarbons, for example benzene, toluene, o-, m- and p-xylenes; or mixtures of solvents of this group; and Group B: aliphatic hydrocarbons, for example pentanes, hexanes, heptanes cyclohexane, benzines, petroleum ethers, water; or mixtures of solvents of this group.

In general, three procedures are possible:

1. The crude chloronitrobenzaldehyde is suspended in a solvent of Group A and a solvent of Group B is added.

The proportion of solids in the suspension of chloronitrobenzaldehyde in the solvent of Group A is generally 10% w/w, preferably 30% w/w, and more preferably 60% w/w, based on the weight of the suspension.

The proportion of solid phase in the suspension is governed to a decisive extent by the content of more readily soluble impurities, especially that of 2-chloro-3-nitrobenzaldehyde.

2. The crude chloronitrobenzaldehyde is suspended in a solvent of Group B and a solvent of Group A is added.

3. The crude chloronitrobenzaldehyde is treated with a mixture of solvents from Groups A and B.

The above statements referring to the content of solid phase in the suspension of chloronitrobenzaldehyde in solvents of Groups A and B also apply to the procedures 2 and 3 in appropriate manner.

The crude chloronitrobenzaldehyde to be treated may be dry or moist, ie it may contain from 0 to 50% w/w, preferably 0 to 100% w/w, of water, based on the weight of chloronitrobenzaldehyde. If present, this content of water must be taken into consideration when using a solvent mixture from Groups A and B. Acetals which are solid at the temperature of treatment, especially the dimethyl acetal and the glycol acetal, may be treated analogously. The temperature used for the treatment generally ranges from −10° C. to +140° C., preferably from 0° to 100° C., more preferably from 10° to 40° C.

The treatment is generally carried out at pH 2 to 12, preferably pH 4 to 10, more preferably pH 6 to 8.

By "crude" chloronitrobenzaldehyde we mean a mixture of the isomers 2-chloro-5-nitrobenzaldehyde and 2-chloro-3-nitrobenzaldehyde, the impurity being substantially the 2-chloro-3-nitrobenzaldehyde present in an amount of from 0.1 to 15% w/w, preferably from 0.1 to 20% w/w, and more preferably from 0.1 to 8% w/w, based on the dry weight of the isomer mixture. Of the corresponding acetals, the dimethyl acetal and the glycol acetal are particularly preferred.

The method of the invention can be executed under atmospheric pressure or an elevated pressure of up to 50 bar, preferably a pressure of from 1 to 10 bar, continuously or batchwise. 50% and preferably 80% of the impurities contained in the crude chloronitrobenzaldehyde isomer mixtures or acetal isomer mixtures are removed therefrom.

It may be necessary to form a compromise between yield and isomeric purity. In general, the yields are between 80 and 95% and the degree of isomeric purity is greater than 98%.

EXAMPLES

Example 1

10 g of a mixture of the isomers 2-chloro-5-nitrobenzaldehyde and 2-chloro-3-nitrobenzaldehyde (GC: 91% v/v 2,5-isomer, 8.7% v/v 2,3-isomer) are suspended in 100 ml of a 1:1 v/v methanol/water mixture, and the suspension is stirred for 30 minutes and filtered in vacuo. There are obtained 8.5 g (93%) of 2-chloro-5-nitrobenzaldehyde (GC: 99.3% v/v 2,5-isomer, 0.7% v/v 2,3-isomer).

Example 2

10 g of a mixture of 2-chloro-5-nitrobenzaldehyde and 2-chloro-3-nitrobenzaldehyde (GC: 91% v/v 2,5-isomer, 8.7% v/v 2,3-isomer) are treated as in Example 1 except that a 1:1 v/v mixture of ethanol and water is used. There are obtained 7.9 g (87%) of 2-chloro-5-nitrobenzaldehyde (GC: 99.9% v/v 2,5-isomer, trace of 2,3-isomer).

Example 3

10 g of a mixture of 2-chloro-5-nitrobenzaldehyde and 2-chloro-3-nitrobenzaldehyde (GC: 91% v/v 2,5-isomer, 8.7% v/v 2,3-isomer) are treated as in Example 1 except that a 1.5:1 v/v mixture of ethanol and water is used. There are obtained 7.4 g (81%) of 2-chloro-5-nitrobenzaldehyde (GC: 99.9% v/v 2,5-isomer, trace of 2,3-isomer).

Example 4

10 g of a mixture of 2-chloro-5-nitrobenzaldehyde and 2-chloro-3-nitrobenzaldehyde (GC: 91% v/v 2,5-isomer, 8.7% v/v 2,3-isomer) are treated as in Example 1 except that a suspension in 50 ml of ethanol is formed, to which 50 ml of water are added dropwise. The suspension is stirred for 25 minutes, cooled to 0° C. and filtered in vacuo. There are obtained 8.6 g (95%) of 2-chloro-5-nitrobenzaldehyde (GC: 99.9% v/v 2,5-isomer, trace of 2,3-isomer).

Example 5

624 g of a mixture of the isomers 2-chloro-5-nitrobenzaldehyde and 2-chloro-3-nitrobenzaldehyde (GC: 91.7% v/v 2,5-isomer, 2.2% v/v 2,3-isomer, other impurities to 100%) are mixed with 1800 g of acetone at 0° C., and 1200 ml of water are added dropwise over a period of 30 minutes. Stirring is continued for 1 hour at 0° C., after which the solids are isolated by filtration in vacuo and then washed with cold water. There are obtained 580 g (99%) of a mixture of the isomers 2-chloro-5-nitrobenzaldehyde and 2-chloro-3-nitrobenzaldehyde (GC: 98.3% v/v 2,5-isomer, 0.3% v/v 2,3-isomer).

Example 6

9 g of a mixture of the isomers 2-chloro-5-nitrobenzaldehyde and 2-chloro-3-nitrobenzaldehyde (GC: 94.1% v/v 2,5-isomer, 5% v/v 2,3-isomer) are mixed with 50 g of methanol at room temperature, and 30 g of petroleum ether are added dropwise over a period of 10 minutes. Stirring is continued for 45 minutes at room temperature and for 30 minutes at 5°–10° C. The solids are isolated by filtration in vacuo and dried. There are obtained 7 g (83%) of 2-chloro-5-nitrobenzaldehyde (GC: 100% v/v 2,5-isomer).

Example 7

2 kg of a mixture of the isomers 2-(2-chloro-5-nitrophenyl)-1,3-dioxolane and 2-(2-chloro-3-nitrophenyl)-1,3-dioxolane [HPLC (LiChrosorb RP 18, 75:25:0.1 v/v/v MeOH/$H_2O$/$H_3PO_4$, 254 nm, 1 ml/min): 94.7% v/v 2,5-isomer, 2.1% v/v 2,3-isomer, other impurities to 100%] are thoroughly washed with 3:1 v/v methanol/water at room temperature, after which the solids are isolated by filtration in vacuo and then dried in vacuo at 40° C. There are obtained 1810 g (95%) of 2-(2-chloro-5-nitrophenyl)-1,3-dioxolane (HPLC: 99.1% v/v 2,5-isomer).

Example 8

(Comparative Example as per DE-A 3,728,926)

174 g of a mixture of the isomers 2-chloro-5-nitrobenzaldehyde and 2-chloro-3-nitrobenzaldehyde (GC: 91.1% v/v 2,5-isomer, 8.7% v/v 2,3-isomer) are mixed with 445 g of distilled water and neutralized with sodium hydroxide. 10 g of benzyldimethyldodecylammonium bromide are added, and the whole is heated under reflux for 30 minutes. The emulsion is then stirred for 2.5 hours at 40° C. The 2-chloro-5-nitrobenzaldehyde which precipitates on cooling to room temperature is isolated by filtration in vacuo and then dried in vacuo. The isomer mixture is regained quantitively (GC: 91.9% v/v 2,5-isomer, 8.1% v/v 2,3-isomer).

We claim:

1. A method of isolating 2-chloro-5-nitrobenzaldehyde or an acetal thereof from a mixture containing 2-chloro-5-nitrobenzaldehyde and at least one isomer thereof wherein the mixture is introduced into a liquid in which the 2-chloro-5-nitrobenzaldehyde is insoluble and the isomers thereof are more readily soluble so as to form a suspension of the 2-chloro-5-nitrobenzaldehyde and a solution of the isomers in the liquid at a temperature of from −10° to +140° C., and separating the suspended 2-chloro-5-nitrobenzaldehyde as a solid from the dissolved isomers thereof.

2. A method as claimed in claim 1, which is carried out at a pH of from 4 to 10.

3. A method as claimed in claim 1, which is carried out at a pH of from 6 to 8.

4. A method as claimed in claim 1, wherein the content of solid isomer mixture in the suspension is from 50% to 99% w/w.

5. A method as claimed in claim 1, wherein the content of solid isomer mixture in the suspension is from 60% to 98% w/w.

6. A method as claimed in claim 1, wherein the content of solid isomer mixture in the suspension is from 70% to 95% w/w.

7. A method as claimed in claim 1, wherein the suspension is formed at a temperature of from 0° to 100° C.

8. A method as claimed in claim 1, wherein the suspension is formed at a temperature of from 10° to 40° C.

* * * * *